US007677248B2

(12) United States Patent
Gerson et al.

(10) Patent No.: US 7,677,248 B2
(45) Date of Patent: Mar. 16, 2010

(54) STIFFENED FILTER MASK

(75) Inventors: Ronald L. Gerson, Carlisle, MA (US); Robert A. Brunell, Forestdale, MA (US); Michael Cupicha, East Schodack, NY (US)

(73) Assignee: Louis M. Gerson Co., Inc., Middleboro, MA (US)

( * ) Notice: Subject to any disclaimer, the term of this patent is extended or adjusted under 35 U.S.C. 154(b) by 1272 days.

(21) Appl. No.: 10/892,933

(22) Filed: Jul. 16, 2004

(65) Prior Publication Data

US 2004/0255946 A1 Dec. 23, 2004

Related U.S. Application Data

(63) Continuation-in-part of application No. 10/423,382, filed on Apr. 25, 2003, now Pat. No. 7,171,967.

(60) Provisional application No. 60/386,297, filed on Jun. 5, 2002.

(51) Int. Cl.
*A61M 11/00* (2006.01)

(52) U.S. Cl. ............................ 128/206.19; 128/205.25

(58) Field of Classification Search ............ 128/205.25, 128/205.29, 206.12, 206.16, 206.18, 206.19, 128/206.21, 206.28, 207.13
See application file for complete search history.

(56) References Cited

U.S. PATENT DOCUMENTS

| | | | | |
|---|---|---|---|---|
| 1,523,884 | A | 1/1925 | LeDuc | 128/146 |
| 411,311 | A | 7/1933 | Leduc | |
| 2,116,241 | A | 5/1938 | Hevmann | 128/139 |
| 2,227,667 | A | 1/1941 | Panettiere | 128/139 |
| 2,556,589 | A | 1/1951 | LeDuc | 128/146 |
| 2,634,734 | A | 4/1953 | Burns | 128/146 |
| RE24,549 | E * | 10/1958 | Haligzer | 128/206.19 |
| 3,042,034 | A | 7/1962 | Gruenewaelder | 128/146 |
| 3,500,825 | A | 3/1970 | Anderson et al. | 128/139 |
| 3,613,678 | A | 10/1971 | Mayhew | 128/146.2 |
| 3,971,369 | A | 7/1976 | Aspelin et al. | 128/146.2 |
| 3,985,132 | A | 10/1976 | Boyce et al. | 128/139 |
| D249,072 | S | 8/1978 | Revoir | D29/8 |
| 4,133,309 | A | 1/1979 | Kohler et al. | 128/146.6 |
| 4,215,682 | A | 8/1980 | Kubik et al. | 128/205.29 |
| 4,245,220 | A | 1/1981 | Johnson | 343/16 R |
| 4,248,220 | A | 2/1981 | White | 128/206.19 |

(Continued)

FOREIGN PATENT DOCUMENTS

| | | |
|---|---|---|
| AU | 709576 | 9/1996 |

(Continued)

OTHER PUBLICATIONS

International Search Report dated Nov. 14, 2005.

*Primary Examiner*—Steven O Douglas
(74) *Attorney, Agent, or Firm*—Occhiuti Rohlicek & Tsao LLP

(57) ABSTRACT

A flat-folding mask includes a filter layer forming a rim. The filter layer has first and second side panels extending from the rim. A substantially centrally located front panel bridges the first and second side panels, the front panel being substantially flat. The filter layer further includes a fused portion that is seamless and spaced from the rim. Triangular pleats may add support to the side walls and increase the effective filtration area of the mask.

69 Claims, 9 Drawing Sheets

U.S. PATENT DOCUMENTS

| | | | | |
|---|---|---|---|---|
| 4,300,549 | A | 11/1981 | Parker | 128/206.19 |
| 4,417,575 | A | 11/1983 | Hilton et al. | 128/206.19 |
| 4,419,993 | A | 12/1983 | Petersen | 128/201.15 |
| 4,419,994 | A | 12/1983 | Hilton | 128/206.19 |
| 4,536,440 | A | 8/1985 | Berg | 428/284 |
| 4,547,420 | A | 10/1985 | Krueger et al. | 428/229 |
| 4,600,002 | A | 7/1986 | Maryyanek et al. | 128/206.19 |
| 4,688,566 | A | 8/1987 | Boyce | 128/206.19 |
| 4,827,924 | A | 5/1989 | Japuntich | 428/206.12 |
| 4,874,339 | A | 10/1989 | Bratz | 445/28 |
| 4,883,547 | A | 11/1989 | Japuntich | 156/73.4 |
| 5,025,506 | A | 6/1991 | Huang | 2/206 |
| 5,232,529 | A | 8/1993 | Miyake | 156/73.4 |
| 5,325,892 | A | 7/1994 | Japuntich et al. | 137/855 |
| 5,699,792 | A | 12/1997 | Reese et al. | 128/206.19 |
| 5,927,280 | A | 7/1999 | Miyake | 128/857 |
| 5,954,055 | A | 9/1999 | Miyake | 128/857 |
| 6,123,077 | A | 9/2000 | Bostock et al. | 128/206.21 |
| 6,125,849 | A | 10/2000 | Williams et al. | 128/206.12 |
| 6,145,504 | A | 11/2000 | Miyake | 128/206.19 |
| 6,332,465 | B1 | 12/2001 | Xue et al. | 128/207.11 |
| 6,336,459 | B1 | 1/2002 | Miyake et al. | 128/857 |
| 6,394,090 | B1 | 5/2002 | Chen et al. | 128/206.12 |
| 6,484,722 | B2 | 11/2002 | Bostock et al. | 128/206.19 |
| 6,536,434 | B1 | 3/2003 | Bostock et al. | 128/206.12 |
| 6,568,392 | B1 | 5/2003 | Bostock et al. | 128/206.21 |
| 6,715,489 | B2 | 4/2004 | Bostock et al. | 128/206.21 |
| 6,722,366 | B2 | 4/2004 | Bostock et al. | 128/206.19 |
| 6,886,563 | B2 | 5/2005 | Bostock et al. | 128/206.19 |
| 7,069,930 | B2 | 7/2006 | Bostock et al. | 128/206.19 |
| 2006/0180152 | A1 | 8/2006 | Bostock et al. | 128/206.12 |

FOREIGN PATENT DOCUMENTS

| | | | |
|---|---|---|---|
| CA | 2213332 | | 9/1996 |
| CA | 2368844 | | 8/2001 |
| CA | 2410260 | | 11/2001 |
| DE | 32 04322 | A1 | 8/1983 |
| EP | 0 281 275 | | 9/1988 |
| EP | 1 118 278 | A2 | 7/2001 |
| EP | 1 147 787 | | 10/2001 |
| EP | 0 814 871 | | 1/2002 |
| EP | 1 258 267 | | 11/2002 |
| FR | 2 853 497 | | 10/2004 |
| GB | 2046102 | | 3/1980 |
| GB | 2 045 093 | A | 10/1980 |
| WO | WO 00/48481 | | 8/2000 |

* cited by examiner

STIFFENED FILTER MASK

CROSS REFERENCE TO RELATED APPLICATIONS

This application is a continuation-in-part of U.S. patent application Ser. No. 10/423,382, filed Apr. 25, 2003, entitled “Face Mask and Method of Manufacturing the Same,” which claims priority from U.S. provisional application Ser. No. 60/386,297, filed Jun. 5, 2002. Each of the above-mentioned applications is hereby incorporated herein by reference.

TECHNICAL FIELD

The present invention relates generally to face masks and, more particularly, the invention relates to face masks used to filter air breathed by people wearing such face masks.

BACKGROUND ART

Air filtration masks (referred to herein as “filter masks”) are widely used to protect people from air borne contaminants and gasses. For example, air borne dust particles are a known hazard commonly on work sites. Consequently, workers normally wear filter masks to avoid inhaling the dust particles. To that end, filter masks used in this application are manufactured with a filter material specified to prevent, among other things, a substantial majority of dust particles from being inhaled by the worker.

In addition to primarily filtering inhaled air, some filter masks are specifically manufactured to filter both inhaled and exhaled air. For example, hospital staff often wear filter masks to prevent both their germs from infecting patients, and patients’ germs from infecting them.

There is a need in the art to improve the filtration efficiency of filter masks. Accordingly, filter masks with a higher efficiency filter layer and/or multiple filter layers have been developed for that purpose. However, this often has the undesirable effect of increasing the air resistance through the filter mask and may cause several problems.

For example, a person wearing the filter mask may have a more difficult time breathing due to the increased air resistance. To overcome this problem while still providing improved filtration efficiency, filter masks have been developed that have an increased filter area. Manufacture of such filter masks, however, can be quite complex. For example, increasing the filter area can cause various portions of the filter layer to overlap or can be costly to construct. Overlap can effectively increase the thickness of the filter layer, thus causing the same air resistance problem as discussed above.

Additionally, since a person wearing the mask while performing manual labor must typically breathe heavier, the filter layer(s) is more likely to flex and eventually collapse around the face. This collapse may cause portions of the face mask to contact and irritate the face of the person wearing the face mask, as well as cause discomfort. Consequently, efforts have been made to stiffen the mask, such as by adding additional material to the filter mask. However, adding additional material to the face mask adds complexity to the production process and increases cost.

SUMMARY OF THE INVENTION

In accordance with one aspect of the invention, a flat-folding mask includes a filter layer forming a rim. First and second side panels extend from the rim to a front panel. A substantially centrally located front panel bridges the first and second side panels, the front panel being substantially flat. The filter layer includes a fused portion spaced from the rim. The fused portion is seamless.

In related embodiments, the filter layer may include a first seam and a second seam extending from the rim. The mask may include a first and second pleat, the front panel bridging the first pleat and the second pleat. The fused portion may be unpleated.

In accordance with another aspect of the invention, a mask includes forms a rim. The filter layer includes a first seam and a second seam extending from the rim. A front panel is positioned between the first seam and the second seam. The filter layer further includes a first and second pleat, the front panel adjoining the first and second pleat. The filter layer includes a fused portion spaced from the rim. The fused portion is seamless.

In related embodiments of the invention, the filter layer may include first and second complimentary portions that form the rim and the front panel, the first portion being connected to the second portion at the first and the second seams. The first and second portions may form any number of side panels that extend from the rim to the front panel. The fused portion may be unpleated.

In embodiments related to the above-described embodiments, the filter layer may have an effective center line that bisects the filter layer in a longitudinal direction, the first and second pleats being substantially bisected by the effective center line. The at least one of the first pleat and the second pleat may form a triangular shape. The first seam may include a first non-linear portion for forming the first pleat, and the second seam may include a second non-linear portion for forming the second pleat. The first and second non-linear portions may be, without limitation, concave or convex.

In further embodiments related to the above-described embodiments, the front panel may be generally parallel to the plane of a face a wearer when the mask is worn by the wearer. The fused portion may substantially define a perimeter of the front panel. The area within the perimeter of the front panel may not include the fused portion. The fused portion may include a first fused portion and a second fused portion positioned within the front panel, the first fused portion and the second fused portion running substantially parallel to each other in a direction latitudinal or longitudinal to the front panel. The fused portion may include at least one fused portion positioned within at least one of the side panels, the fused portion extending substantially from the rim to the front panel. The side panels may include a top side panel, a bottom side panel, a right side panel, and a left side panel. The mask may be capable of forming a cup-shaped air chamber over a nose and a mouth of a wearer, and/or may be capable of being folded flat for storage. At least one layer of material may be attached to the filter layer, which may include spunbonded polypropylene or olefin. The filter layer may be a single, contiguous sheet of material. The mask may further include a valve attached to the front panel. A support base may support the filter layer.

In still further embodiments related to the above-described embodiments, the filter layer may include a first tab and a second tab that extend seamlessly from the rim. A head strap may be attached to the first tab and the second tab. The tabs may be generally perpendicular to the front panel when the rim of the mask is pulled open. The filter layer may form at least two side panels that extend from the rim to the front panel, the first tab and the second tab extending from the same side panel.

In accordance with yet another aspect of the invention, a method of manufacturing a mask includes forming, in a sheet or laminate of filter material, one or more stiff portions relative to another portion of the filter material. The filter material is folded to form two sections, each section having two ends. The two ends of each section are reshaped to form two reshape lines. The two sections are then connected along the two reshape lines such that the two sections form a rim. The two sections extend from the rim to form an unpleated central portion when the mask is in use. The unpleated central portion includes at least one of the one or more stiff portions.

In accordance with still another aspect of the invention, a method of manufacturing a mask having a filter layer includes folding the filter layer to form two sections, each section having two ends and one side. The two ends of each section are reshaped to form two reshape lines, each of the two reshape lines having a non-linear portion. The two sections are connected along the two reshape lines such that the two sections form a pocket having a rim, the rim extending to a front panel when the pocket is open.

In accordance with another aspect of the invention, a method of manufacturing a mask having a filter layer includes forming a fused portion in the filter layer, the fused portion being seamless. Two planar surfaces of the filter layer are connected to form a pocket having a rim. The rim is pulled on to open the pocket, the filter layer forming at least three side panels that extend from the rim to define a perimeter of a front panel.

In accordance with yet another aspect of the invention, a mask includes a filter layer forming a rim. The filter layer includes a front panel. At least one side panel extends from the rim to the front panel. A first tab and a second tab extend seamlessly from the rim.

In related embodiments, the front panel is substantially flat. The mask may further include a head strap attached at the first tab and the second tab. The first tab and the second tab may be capable of being folded substantially near the rim, and may be generally perpendicular to the front panel when the rim of the mask is pulled open. The filter layer may form at least two side panels that extend from the rim to the front panel, the first tab and the second tab extending from the same side panel.

In accordance with still another embodiment of the invention, a flat-folding mask includes a rim. A substantially flat front panel is spaced from the rim and is substantially centrally positioned. A seamless fused portion is spaced from the rim. The mask is capable of folding substantially flat when not in use, and opening for use after being folded flat. The mask when open forms a recess defined by the rim.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

In illustrative embodiments of the invention, portions of an air filtration mask (hereinafter "filter mask" or "mask") are stiffened without adding additional material to the mask. This stiffening aids in preventing the mask from collapsing around the face, and also tends to keep the mask in a desired form. The filter mask may advantageously have an increased filtration area by incorporating two pleats, which may be triangular in shape, into its filter layer. Moreover, manufacturing is simplified because, among other things, much of the process of manufacturing the filter mask may be completed while the filter layer is laid flat. Details of illustrative embodiments are discussed below.

Figure 1A:
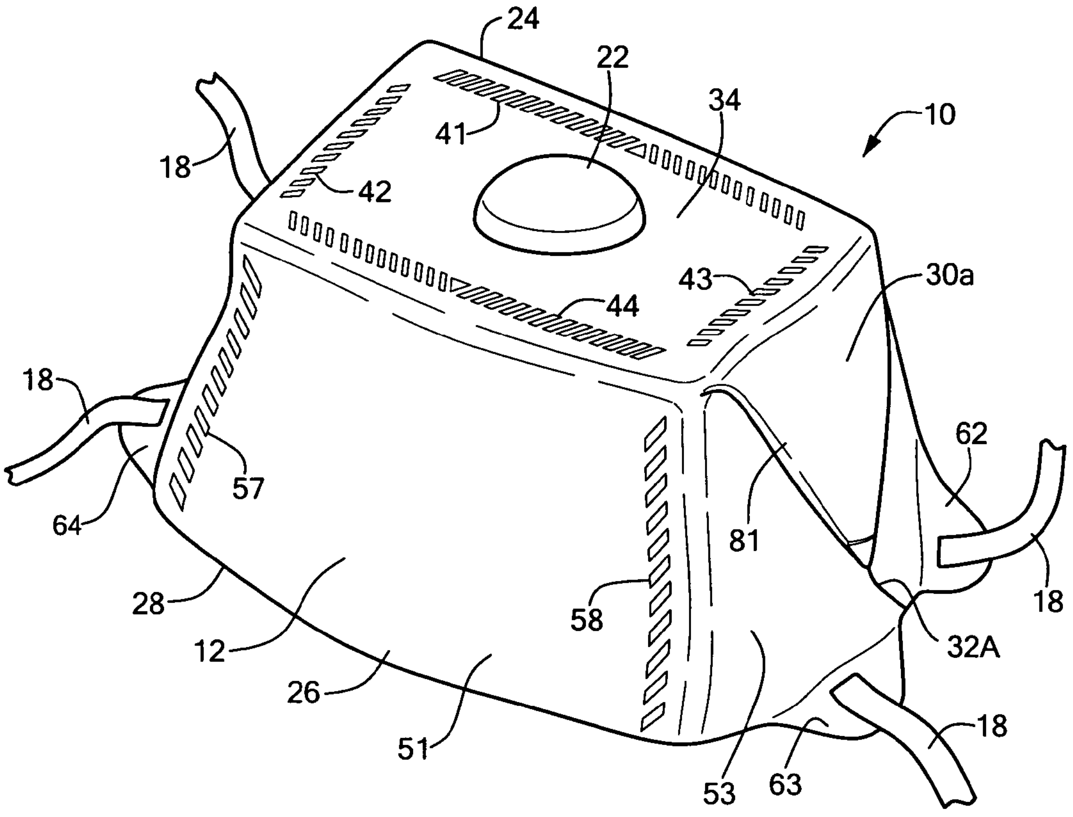
FIG. 1*a* schematically shows an exemplary filter mask constructed in accordance with illustrative embodiments of the invention.

FIG. 1*a* schematically shows an exemplary filter mask 10 constructed in accordance with illustrative embodiments of the invention. Specifically, the filter mask 10 includes a specially constructed filter layer 12 that is capable of opening to form a concave area for receiving, and forming a seal over, a user's nose and mouth (see FIG. 2). The filter layer 12 includes at least one side panel 50-53, for example, a top side panel 50 (see FIG. 2), a bottom side panel 51, a left side panel 52 and a right side panel 53, that extend from a rim 28 to a front panel 34. As described in more detail below, the filter layer 12 may also include one or more pleats 30A and 30B.

In various embodiments, the front panel 34 is substantially flat and may be substantially parallel to the plane of the face when worn. Moreover, in illustrative embodiments, the front panel 34 is substantially centrally located on the mask. For example, as shown in FIG. 2, the center of the front panel 34, which borders each of the side panels 50-53, may be positioned substantially at, or include, the center of the mask 10 when opened (e.g., the intersection of the mask's central longitudinal axis and central latitudinal axis).

Figure 1B:
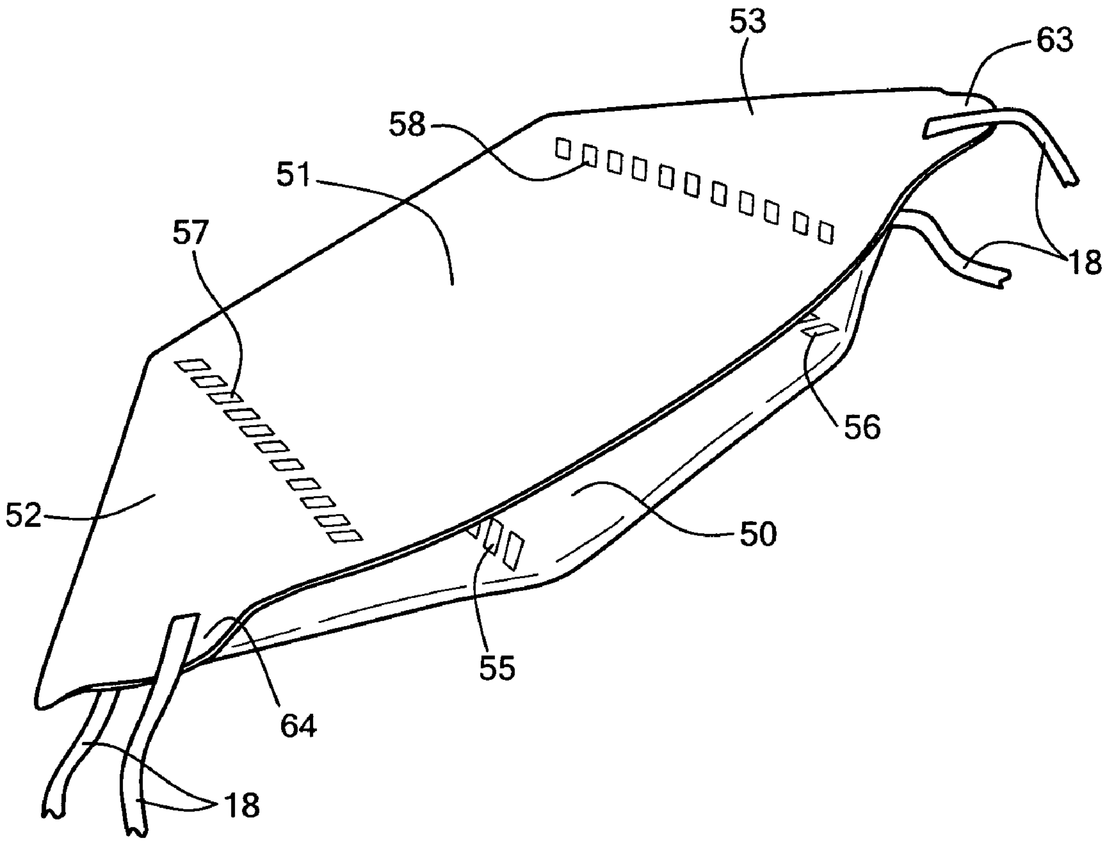
FIG. 1*b* schematically shows the mask shown in FIG. 1*a* in a folded position.
Figure 2:
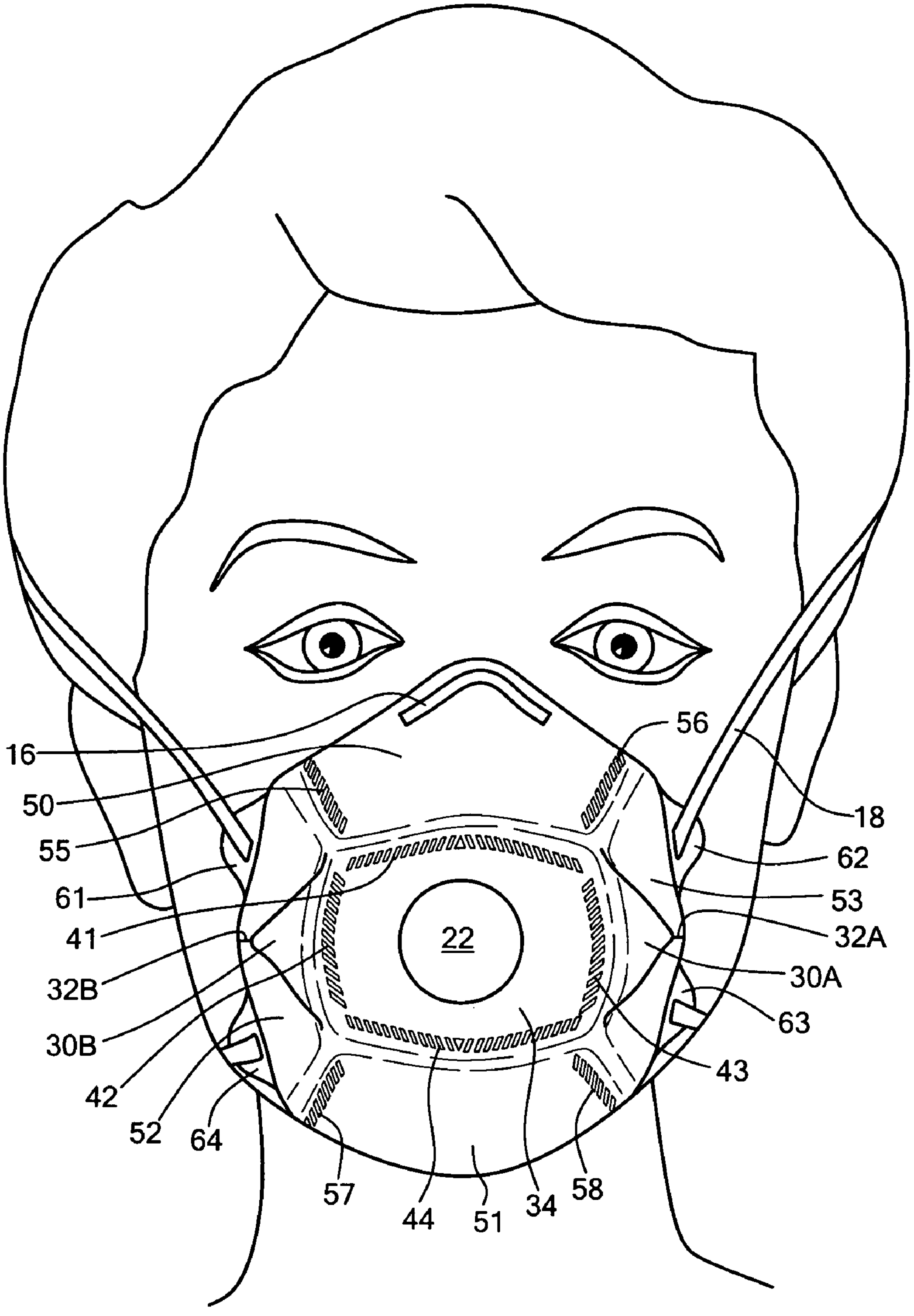
FIG. 2 schematically shows a person wearing the mask shown in FIG. 1*a*.

In various embodiments, the filter mask 10 may include a nose piece 16 to properly position the mask 10 against the user's nose, and straps 18 to secure the mask 10 to the user's face, as shown in FIGS. 1 and 2. Additionally, the filter mask 10 may also include a one-way valve 22 that more freely permits air to be exhaled. Of course, illustrative embodiments permit air to be freely inhaled through the filter layer 12. The valve 22 may be any valve known in the art conventionally used for these purposes, such as a one-way flapper valve.

The straps 18 may be constructed from a resilient rubber material or other conventionally known material (e.g., a non-resilient fabric), that permits a secure and snug fit between the user's face and the rim 20. The straps 18 thus apply an inwardly directed force for those purposes. At a minimum, this force should be sufficient at least to hold the mask 10 to the user's face. Moreover, it is preferred that the rim 20 have a contoured surface that contours to the user's face. Accordingly, when the straps 18 apply the noted inwardly directed force to the mask 10, the contoured surface should be sufficiently flexible and resilient to shape to the user's face. This ensures that the substantial majority of the user's air is inhaled and exhaled through the filter mask 10. In some embodiments, the rim 20 includes additional material (e.g., rubber) to provide an effective seal against the user's face.

FIG. 1*b* schematically shows the mask 10 of FIG. 1*a* in a folded position. The top panel 50 and bottom panel 51 are capable of folding onto the front panel 34, such that the mask 10 becomes substantially flat. This advantageously allows for convenient storage of the mask 10. For example, the mask 10 may be folded flat and placed in a shirt pocket.

In illustrative embodiments of the invention, the filter layer 12 is made of a filter material that includes one or more fused portions 41-44 and 55-58 that serve to stiffen the filter material. Furthermore, the fused portions 41-44 and 55-58 are seamless, i.e., they are not used to secure two or more edges of the filter layer 12 together. Rather, the primary purpose of the stiff portions 42-46 is to aid in maintaining a desired shape of the mask 10 and/or prevent the mask 10 from collapsing against a user's face. The fused portions 41-44 and 55-58 are spaced from the rim. It is to be understood that the fused portions 41-44 and 55-58 are in addition to any stiffened portions of the filter layer 34 that are positioned on or substantially close to the rim 28 for the purposes of stiffening the rim 28.

In various embodiments, the fused portions 41-44 are formed, without limitation, by ultrasonic welding and/or applying heat. The fused portions 41-44 and 51-58 of the filter material typically do not include any additional material and are not pleated. Furthermore, the fusing of the material may be performed while the filter layer is laid flat. As a result, the manufacturing process for stiffening the mask 10 is simplified and costs are minimized. Details of an exemplary manufacturing process for forming the face mask 10 is discussed below with reference to FIG. 3.

At least one of the fused portions 41-44 may be positioned within the front panel 34 of the mask 10, helping to shape the front panel 34 of the mask and prevent the front panel 34 from collapsing on the person's face. For example, the fused portions 41-44 positioned within the front panel 34 may substantially define the perimeter of the front panel 34, such that the flat panel 34 remains generally flat. The area of the front panel 34 within the perimeter defined by the fused portions 41-44 may not include any fused portions. In various embodiments, the area of the front panel 34 within the perimeter defined by the fused portions 41-44 may have a contiguous portion, encompassing more than 50% of the area of the front panel 34 that does not include any fused portions.

The fused portions in the front panel 34 may form a perimeter having various shapes, such as, without limitation, a triangle, a square, a rectangle, a rhombus, or a circle. In illustrative embodiments, the front panel 34 may include, without limitation, first and second fused portions 41 and 44 that run parallel to each other in a direction longitudinal to the front panel 34. Alternatively, or in combination with stiff portions 41 and 44, the front panel 34 may include third and fourth stiff portions 42 and 42 that run parallel to each other in a direction latitudinal to the front panel 34.

One or more of the fused portions 55-58 may be positioned within at least one of the side panels 50-53, in addition to, or in combination with, the fused portions on the front panel 34. The fused portions 55-58 may extend substantially from the rim 28 to the front panel 34, such that they support and, in various embodiments, contribute in defining the shape of the side panels 50-53. Accordingly, the fused portions 55-58, particularly when combined with stiff portions on the front panel 34, may be placed such that they tend to form an air chamber which stands away from a face of a person when the mask 10 is in use. Consequently, a molded support base that supports the filter layer 12 is not necessary to provide such a shape. The air chamber formed may be of various geometric shapes, such as, without limitation, a triangle, a square, a rectangle, a rhombus, or a circle.

The filter layer 12 may be constructed from two complimentary portions 24 and 26 that together form both 1) the filter layer rim 28, and 2) a pair of pleats 30A and 30B. As known by those in the art, pleats are formed by a portion of the filter material that is normally folded over on itself. Although the pleats may be single pleats (one fold), illustrative embodiments include double pleats (two folds). The pleats 30A and 30B desirably increase the surface area of the filter layer 12, consequently improving filtering efficiency without requiring multiple filter layers. Alternatively, the increased filter area may allow a specified filtration efficiency to be achieved with a lighter weight filter material layer, thereby also providing a lower breathing resistance and increased user comfort. In illustrative embodiments, other than portions of the pleats 30A and 30B, the entire filter layer 12 is substantially free of overlap. In other words, portions of the filter layer 12 do not overlap other portions. As known by those skilled in the art, being substantially free of overlap is beneficial because that typically increases air resistance through the filter mask 10. Furthermore, the triangular pleats 30A and 30B may remain substantially unsealed along their folded edges 81, thereby effectively doubling the filtering area that the pleats provide.

It should also be noted that the triangular pleats 30A and 30B are formed from a portion of the filter material that would typically, when manufacturing a similar mask with no pleats, be cut from a sheet of filter material and discarded. Thus, in preferred embodiments of the invention, the triangular pleats 30A and 30B are formed without added material cost.

The complimentary portions 24 and 26 of the filter layer 12 illustratively are mirror images of each other. Accordingly, the top portion 24 and bottom portion 26 are considered to meet along an effective center line that bisects the entire filter layer 12. This effective center line also is substantially coincident with a pair of seams 32A and 32B that each extend from the filter layer rim 28 to one of the pleats 30A and 30B. The pleats 30A and 30B are bridged via the front panel 34 of the filter layer 12 that also is bisected by the effective center line. In a similar manner, the effective center line also bisects both pleats 30A and 30B. In practice, however, it is expected that manufacturing tolerances may not permit every filter mask 10 to have exactly bisected/coincident filter layer portions. Those filter masks having filter layer portions that are not exactly bisected/coincident, but very close to being bisected/coincident, also should be considered to be within the scope of various embodiments of the invention.

Figure 3:
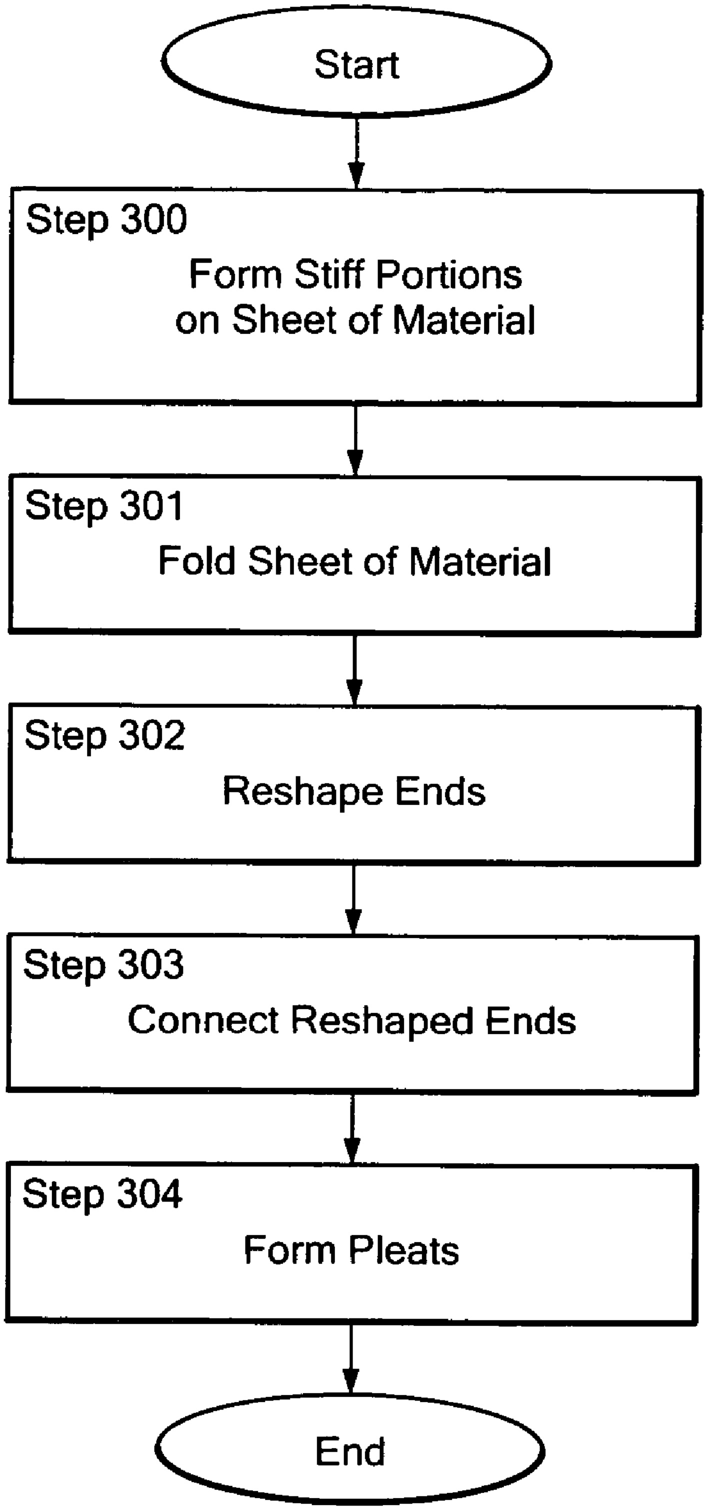
FIG. 3 shows a process of manufacturing the mask shown in FIG. 1*a* in accordance with illustrative embodiments of the invention.

FIG. 3 shows a process of manufacturing the filter mask 10 shown in FIGS. 1 and 2. It is to be understood that the order of the process steps shown in FIG. 3 may vary.

Figure 4:
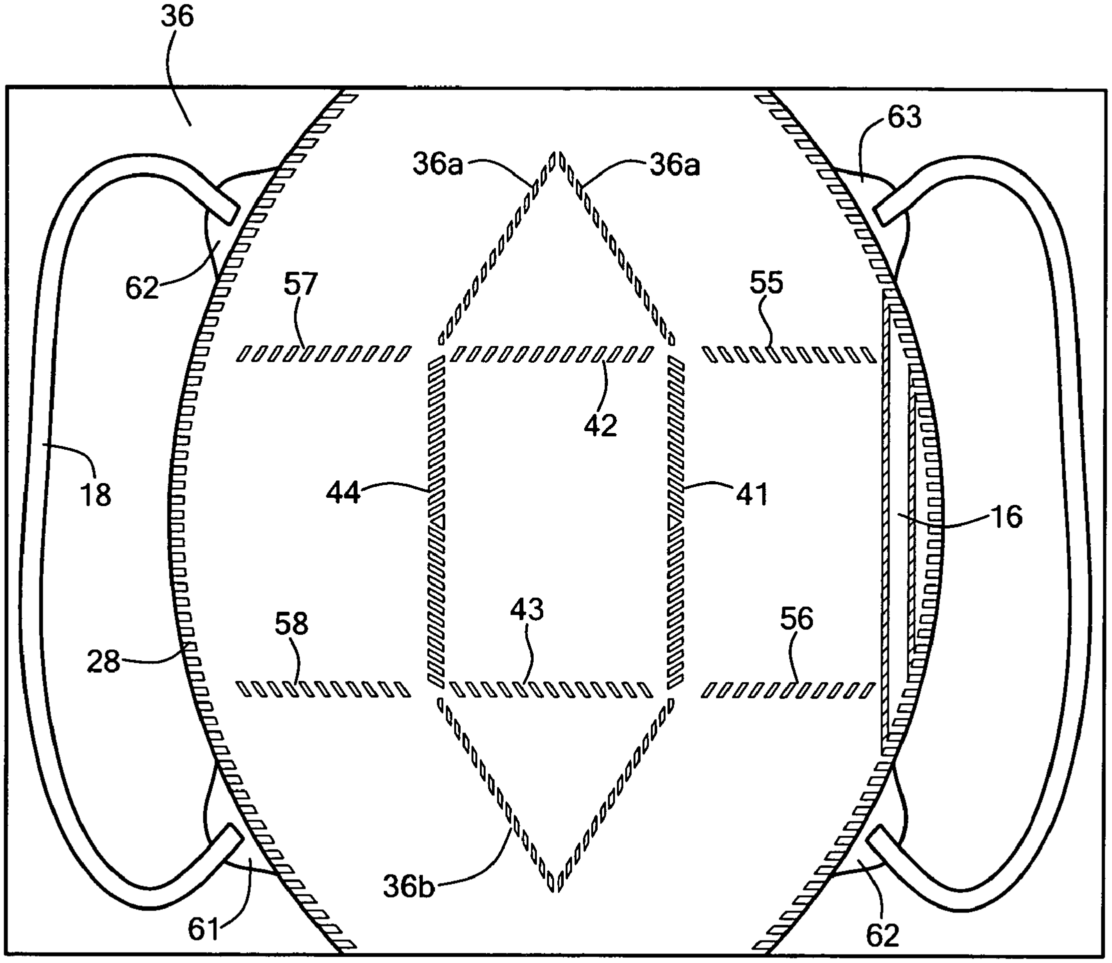
FIG. 4 schematically shows a sheet of filter material that includes stiffened portions in accordance with illustrative embodiments of the invention.

The process begins at step 300, in which the fused portions 41-44 and 55-58 are formed in a sheet of filter material 36. Particularly, as shown in FIG. 4, the sheet of filter material 36 may be laid flat on a surface, after which the seamless, fused portions 41-44 and 55-58 may be formed, without limitation, by ultrasonic welding and/or the application of heat. Of course, the fused portions are not limited to 41-44 and 55-58, and may be added elsewhere where desired, such as on pleats 30*a* and 30*b*.

The filter layer 12 may be manufactured from any conventionally known filter material used for such purposes. The appropriate filter material, however, is selected based upon the intended use of the mask 10. Specifically, the filter material is selected based upon the material characteristics (i.e., filter efficiency, porosity, etc . . . ) required for the intended use. For example, the filter layer 12 may be constructed from polypropylene melt-blown web manufactured to provide a respirator mask with the filtration efficiency and breathing resistance to comply with the well known N100 NIOSH (National Institute of Safety and Health) standard. Details of the N100 NIOSH standard can be obtained from NIOSH, which has a World Wide Web site address of http://www.cdc.gov/niosh/homepage.html.

As another example, the filter layer 12 may be constructed from polypropylene melt-blown web manufactured to provide a respirator mask to comply with the well known P3SL CE (Community European) standard, EN 149:2001. Of course, other types of materials may be used. Accordingly, discussion of specific types of materials is exemplary for many embodiments and thus, not intended to limit all embodiments of the invention. Those skilled in the art should understand which other types of materials may be used.

Figure 5:
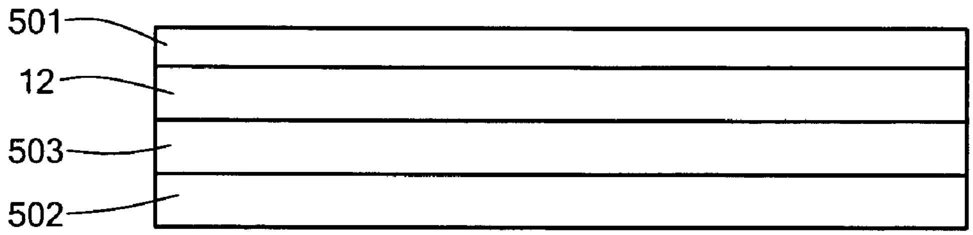
FIG. 5 schematically shows a filter layer overlaid with other layers of material in accordance with illustrative embodiments of the invention.

Furthermore, the filter layer 12 may be overlaid with other layers of material to form, for example, a laminate. The other layers of material may include, for example, an outer layer 501, an inner layer 502, and/or a stiffening layer 503, as shown in FIG. 5. The outer and inner layer 501 and 502 may be made, without limitation, of spunbonded polypropylene so as to provide a smooth outside surface, while the stiffening layer 503 may be made of a stiffening material such as spunbonded olefin. It is to be understood that the layers of materials may be formed as an integral sheet of material prior to step 300. Alternatively, the various layers of materials may be attached by various means known in the art including, without limitation, during any fusing occurring in step 300. It is to be further understood that the stiffening in step 300 may be performed on any or all layers of the laminate: however for exemplary purposes the subject manufacturing process is described with regard to a single filter layer 12.

While the sheet of material 36 is laid flat, the filter layer 12 may be trimmed where desired to form what will become the rim 28. Additionally, the head straps 18 and nose piece 16 may be attached to the sheet of material 36.

In illustrative embodiments, the sheet of material 36 may be trimmed to form tabs 61-64 for attaching headstraps 18. The head straps 18 may be attached to the tabs 61-64 using various means in the art, such as by being bonded, welded, sewn, glued, fastened, and/or heated. The tabs 61-64, which extend seamlessly from the rim 28, may be positioned in a spaced configuration around the rim 28, thereby spreading the moments of force of the head straps 18 over the rim of the mask 10. This results in greater comfort when wearing the mask, and a more uniform seal of the rim 28 to the wearer's face. In use, the tabs 61-64 may be folded, and/or may be generally perpendicular to the front panel 34 so as to conform to the face of the wearer.

Figure 6:
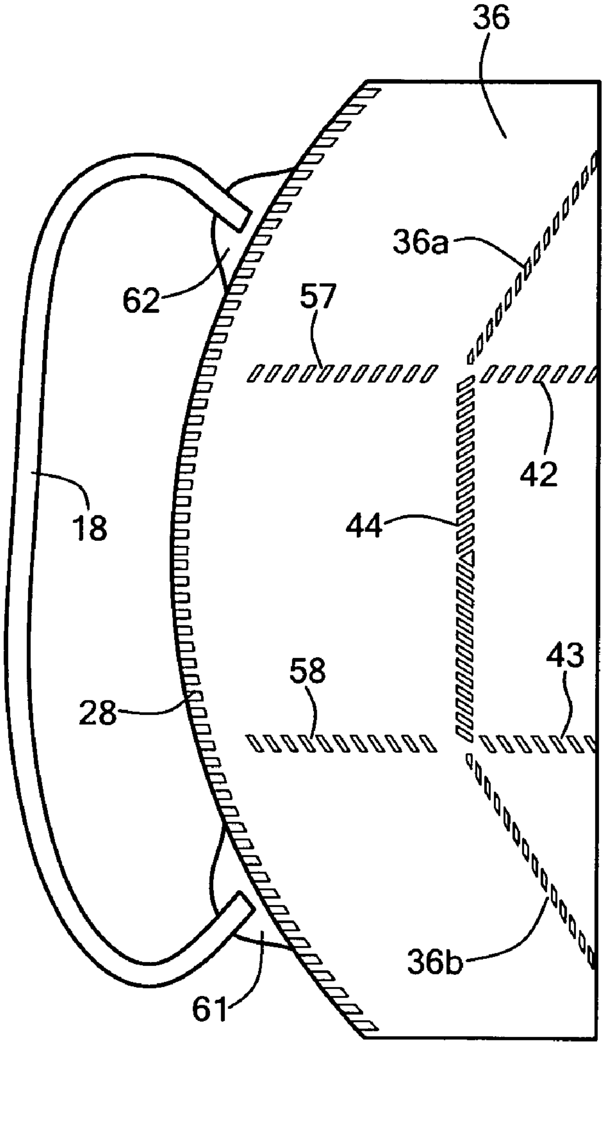
FIG. 6 schematically shows a folded sheet of filter material laid flat on a surface in accordance with illustrative embodiments of the invention.

The process then continues to step 301, in which the sheet of filter material 36 is folded. More specifically, the filter material may be folded along its longitudinal center 42 to form two sections, with each section having two ends. The entire folded sheet is preferably laid flat on a surface, to obtain the configuration shown in FIG. 6, with each section having two ends. Note that only one section 601 with ends 602*a* and 602*b* is visible in FIG. 6.

Figure 7:
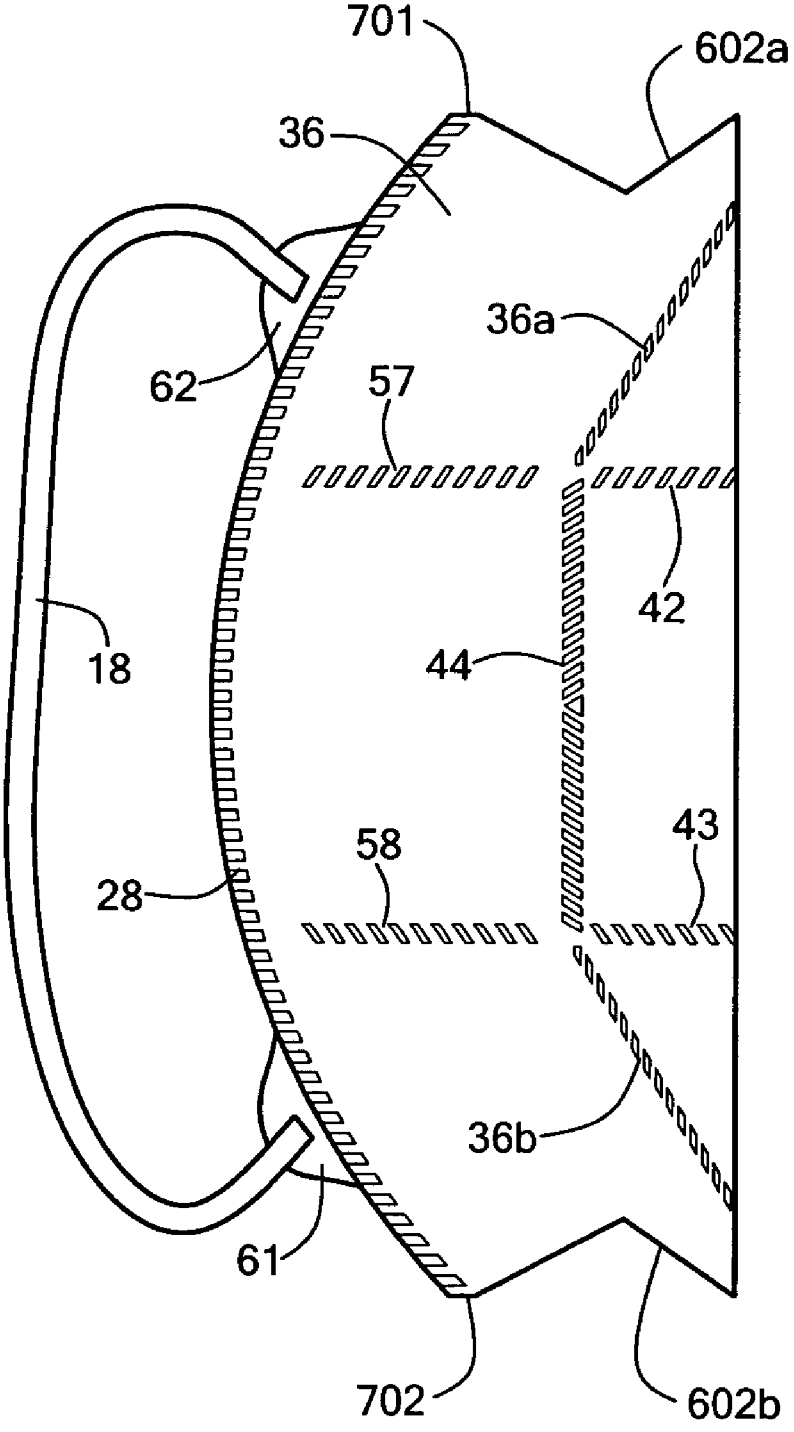
FIG. 7 schematically shows a folded sheet of material with reshaped ends, in accordance with illustrative embodiments of the invention.

Once flat, the process continues to step 302, in which the ends 602*a* and 602*b* of the folded sheet of filter material are reshaped. Specifically, while folded, the two ends 602*a* and 602*b* of the folded sheet are cut in a predetermined manner. In illustrative embodiments, the two ends 602*a* and 602*b* are cut to form the configuration shown in FIG. 7. The reshaped ends 602*a* and 602*b* may be non-linear, so that, without limitation, a triangular pleat can easily be formed, as described below in more detail. For example, the reshaped ends 602*a* and 602*b* may include a concave or convex portion. In alternative embodiments, the ends 602*a* and 602*b* of the folded filter material may be reshaped in a different manner, or left in their original form.

After the ends are reshaped, the edges of the filter material are connected along the reshape lines (step 303). Any known connecting method may be used. For example, the edges may be ultrasonically bonded, welded, sewn, glued, fastened, and/or heated to connect the edges, as known in the art, to form seams 701 and 702.

The process then continues to step 304, in which the pleats 30*a* and 30*b* are formed. This may be accomplished by opening the mask 10, such as by pulling on rim 28, and folding ends 701 and 702 of the reshaped lines down. The pleats 30*a* and 30*b* may then be connected to portions of left side panel 52 and right side panel 53 respectively to form the exemplary filter mask 10 illustrated in FIGS. 1 and 2. The pleats 30*a* and 30*b* advantageously add structural support to side panels 52 and 53, respectively, thus increasing the durability of the mask 10. Furthermore, the pleats 30*a* and 30*b* may be attached to the side panels 52 and 53 at distal ends 701 and 702 such that the pleats 30*a* and 30*b* are substantially open on their undersides as well as on their top sides to provide greater filtration area. In various embodiments, these pleats may increase the effective surface of the respirator by approximately 15%-20%. The pleats 30*a* and 30*b* may be connected to the side panels 52 and 53 of the mask 10 using various methods known in the art, such as by bonding, welding, sewing, gluing, fastening, and or heating.

Accordingly, among other things, the filter mask 10 has two portions that form a rim 28 and that are connected by first and second seams 701 and 702. The first seam 701 extends from the rim 28 and is partially covered by the first pleat 30*a*, and the second seam 702 extends from the rim 28 and is partially covered by the second pleat 30*b*. The first and second shaped pleats 30*a* and 30*b*, which in the embodiments shown are triangular in shape, are connected via the front panel 34. The fused portions 41-44 stiffen, and define the perimeter of the substantially flat, front panel 34, while the fused portions 55-58 help strengthen and define the side panels 50-53 to form a foldable cup shaped mask 10 that extends away from the face.

Figure 8A:
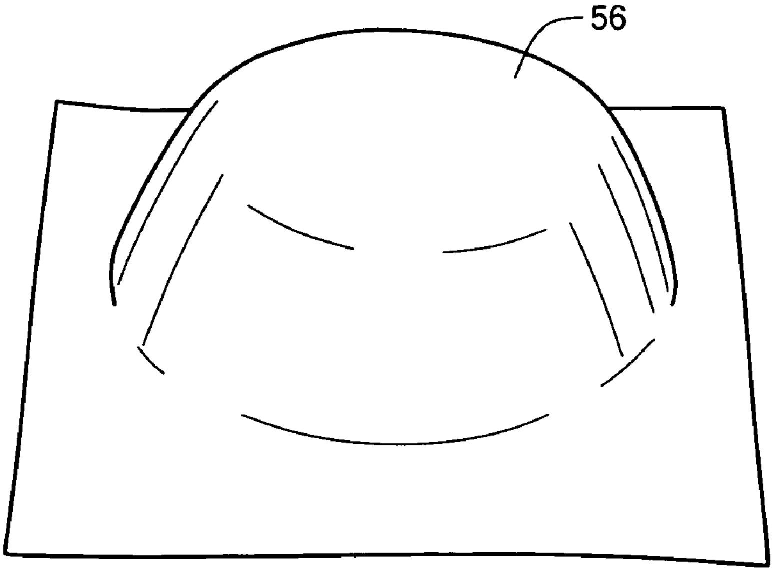
FIG. 8*a* schematically shows a plan view of a support base used in illustrative embodiments of the invention.
Figure 8B:
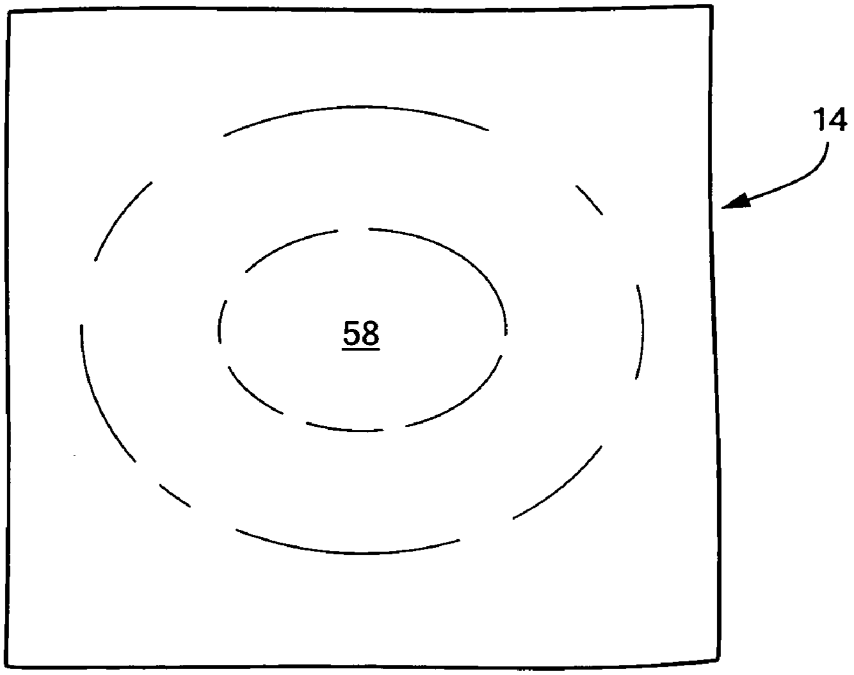
FIG. 8*b* schematically shows a bottom view of the support base shown in FIG. 8*a*.

The mask 10 may optionally be coupled to a support base 14. To that end, the concave portion of the mask 10 is placed over a convex portion 56 of the support base 14. FIG. 8A schematically shows a perspective top view of the support base 14 and its convex portion 56, while FIG. 8B schematically shows a bottom view of the support base 14 (i.e., a concave portion formed by the convex portion). In some embodiments, the inner surface of the concave portion 55 of the secondary assembly 54 is substantially flush against the outer surface of the convex portion 56 of the support base 14.

The mask 10 may be coupled with the support base 14 in a number of ways. In some embodiments, the filter layer rim 28 is welded to a corresponding area of the support base 14. It should be noted that in a manner similar to the reshape lines (discussed above with regard to FIG. 304), any manner known in the art for coupling the support base 14 to the secondary assembly 54 should suffice. The support base 14 illustratively is manufactured from a porous polyester that more resilient than the filter material. In other embodiments, this relative resilience is not necessary. The support base 14 material illustratively introduces no more than a negligible air resistance to the overall filter mask 10.

Figure 9:
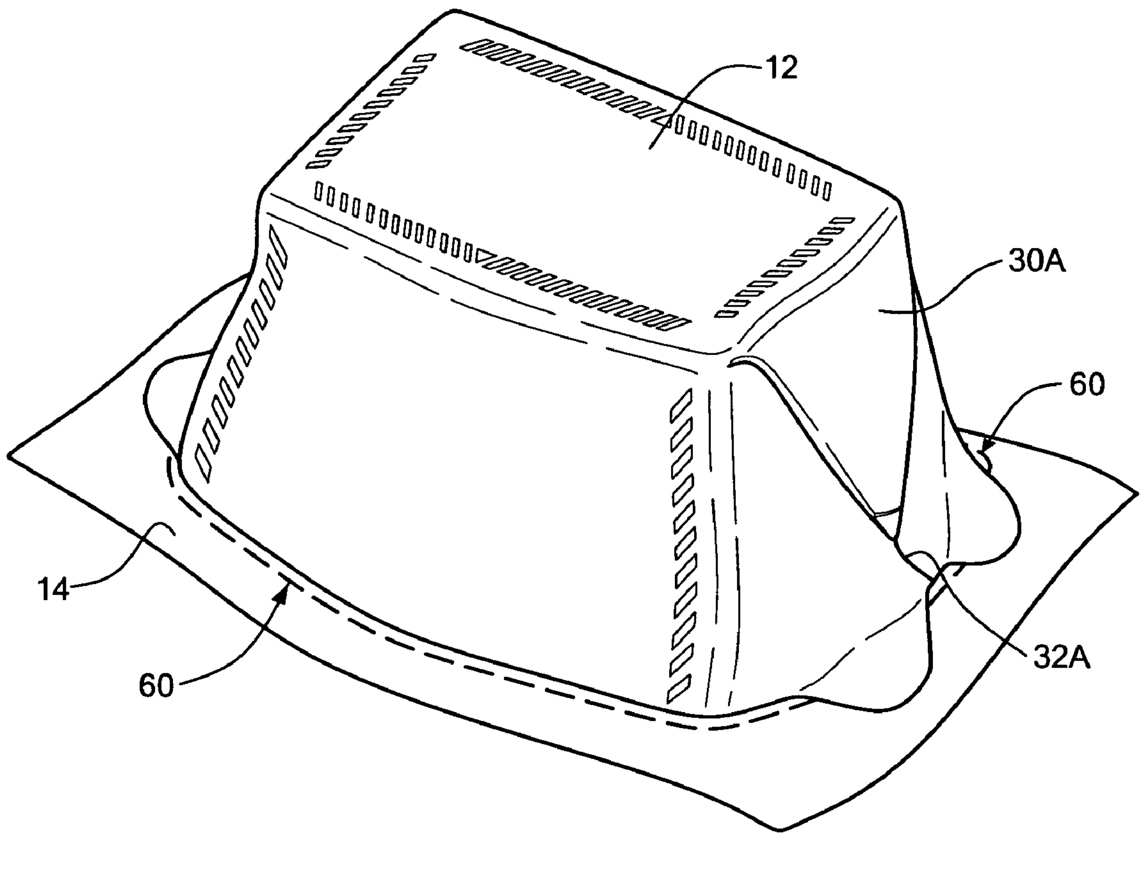
FIG. 9 schematically shows the filter mask coupled to the support base of FIGS. 8*a* and 8*b*.

After coupling the support base 14 to the support base. final manufacturing steps may be performed. In particular, excess material may be removed from the support base 14 along the line identified by reference number 60 in FIG. 9. In illustrative embodiments, about ⅛ of an inch of base material extends beyond the area that connects the mask 10 to the support base 14. This extra material and the connection area together may form a rim 20, which has a surface that is flexible enough to contour to a user's face. In addition to removing excess material, the straps 18, nose piece 16, and valve 22 may be added now, if not done previously, thus completing the process.

When in use, as shown in FIG. 2, the mask 10 is placed over a person's nose and mouth. The straps 18 may wrap together behind the person's head, thus providing the necessary force to both hold the mask 10 to the person's face and contour the rim 28 to such person's face. The person may breath normally and without stress (caused by the mask 10).

Although various exemplary embodiments of the invention have been disclosed, it should be apparent to those skilled in the art that various changes and modifications can be made that will achieve some of the advantages of the invention without departing from the true scope of the invention. These and other obvious modifications are intended to be covered by the appended claims.

What is claimed is:

1. A flat-folding mask comprising:

a filter layer forming a rim and having:

first and second side panels extending from the rim;

a substantially centrally located, substantially flat front panel bridging the first and second side panels;

a first pleat adjoining the front panel; and a fused portion spaced from the rim, the fused portion being seamless, wherein the first side panel is a top side panel, the second side panel is a bottom side panel, the mask further comprising a right side panel and a left side panel.

2. The mask according to claim 1, wherein the filter layer further comprises a first seam and a second seam extending from the rim.

3. The mask according to claim 1, further comprising a second pleat, the front panel bridging the first pleat and the second pleat.

4. The mask according to claim 3, wherein the wherein the filter layer further comprises a first and second seam, the first seam including a first non-linear portion for forming the first pleat, and the second seam includes a second non-linear portion for forming the second pleat.

5. The mask according to claim 3, wherein the filter layer has an effective center line that bisects the filter layer in a longitudinal direction, the first and second pleats being substantially bisected by the effective center line.

6. The mask according to claim 3, wherein at least one of the first pleat and the second pleat form a triangular shape.

7. The mask according to claim 1, wherein the fused portion substantially defines a perimeter of the front panel.

8. The mask according to claim 7, wherein the front panel within the perimeter does not include the fused portion.

9. The mask according to claim 1, wherein the front panel is generally parallel to the plane of a face a wearer when the mask is worn by the wearer.

10. The mask according to claim 1, wherein the fused portion includes a first fused portion and a second fused portion positioned within the front panel, the first fused portion and the second fused portion running substantially parallel to each other in a direction longitudinal to the front panel.

11. The mask according to claim 10, wherein the fused portion includes a third fused portion and a fourth fused portion positioned within the front panel, the third fused portion and the fourth fused portion running substantially parallel to each other in a direction latitudinal to the front panel.

12. The mask according to claim 1, wherein the fused portion includes a first fused portion and a second fused portion positioned within the front panel, the first fused portion and the second fused portion running substantially parallel to each other in a direction latitudinal to the front panel.

13. The mask according to claim 1, wherein the fused portion includes at least one fused portion positioned within the first and second side panel, the at least one fused portion extending substantially from the rim to the front panel.

14. The mask according to claim 1, wherein during use the mask is capable of forming a cup-shaped air chamber over a nose and a mouth of a wearer.

15. The mask according to claim 1, wherein the fused portion is unpleated.

16. The mask according to claim 1, further comprising at least one layer of material attached to the filter layer.

17. The mask according to claim 16, wherein the at least one layer of material includes spunbonded polypropylene.

18. The mask according to claim 16, wherein the at least one layer of material includes olefin.

19. The mask according to claim 1, wherein the filter layer is a single, contiguous sheet of material.

20. The mask according to claim 1, further comprising a valve attached to the front panel.

21. The mask according to claim 1, further comprising a support base that supports the filter layer.

22. The mask according to claim 1, wherein the filter layer further includes a first tab and a second tab that extend seamlessly from the rim.

23. The mask according to claim 22, the mask further comprising:

a headstrap attached to the first tab and the second tab.

24. The mask according to claim 22, wherein the tabs are generally perpendicular to the front panel when the rim of the mask is pulled open.

25. The mask according to claim 22, wherein the filter layer forms at least two side panels that extend from the rim to the front panel, the first tab and the second tab extending from the same side panel.

26. A mask comprising:

a filter layer forming a rim, the filter layer including:

first and second side panels extending from the rim, a first seam and a second seam extending from the rim, a substantially flat front panel between the first seam and the second seam, a first pleat and a second pleat, the front panel adjoining the first and second pleat, wherein the filter layer includes a fused portion being seamless and spaced from the rim, and the first side panel is a top side panel, the second side panel is a bottom side panel, the mask further comprising a right side panel and a left side panel.

27. The mask according to claim 26, wherein the front panel is generally parallel to a face of a wearer when the mask is worn by the wearer.

28. The mask according to claim 26, wherein the mask is capable of being folded flat for storage.

29. The mask according to claim 26, further comprising a support base that supports the filter layer.

30. The mask according to claim 29, wherein the support base forms a base rim, the rim of the filter layer being secured to the base rim.

31. The mask according to claim 29, further comprising a valve extending through the filter layer and the support base.

32. The mask according to claim 26, further comprising at least one layer of material, the at least one layer of material and the filter layer being attached.

33. The mask according to claim 26, wherein the filter layer is a single sheet of material.

34. The mask according to claim 26, wherein the filter layer includes first and second complimentary portions that form the rim and the front panel, the first portion being connected to the second portion at the first and the second seams.

35. The mask according to claim 34, wherein the first and second portions further form the top side panel and the bottom side panel, the top side panel and the bottom side panel extending from the rim to the front panel.

36. The mask according to claim 35, wherein the first and second portions further form the left side panel that includes the first seam and the right side panel that includes the second seam, the first pleat folded over the left side panel, and the second pleat folded over the right side panel.

37. The mask according to claim 36, wherein the first pleat extends from the front panel towards the rim and is attached to the left side panel, and wherein the second pleat forms a second fold that extends from the front panel towards the rim and is attached to the right side panel.

38. The mask according to claim 26, wherein the fused portion includes at least one fused portion that extends substantially from the rim to the front panel, such that the mask stands away from the rim.

39. The mask according to claim 26, wherein the fused portion includes at least one fused portion that is positioned within the front panel.

40. The mask according to claim 39, wherein the fused portion positioned within the front panel substantially forms at least one of a rectangle, a square, a rhombus, and a circle.

41. The mask as defined by claim 26, wherein the filter layer has an effective center line that bisects the filter layer in a longitudinal direction, the first and second seams being substantially coincident with the effective center line.

42. The mask as defined by claim 26, wherein the filter layer has an effective center line that bisects the filter layer in a longitudinal direction, the first and second pleats being substantially bisected by the effective center line.

43. The mask according to claim 26, wherein the filter layer further includes a first tab and a second tab that extend seamlessly from the rim.

44. The mask according to claim 43, wherein the mask further includes:

a head strap attached to the first tab and the second tab.

45. The mask according to claim 43, wherein the tabs are generally perpendicular to the front panel when the rim of the mask is pulled open.

46. The mask according to claim 43, wherein the filter layer forms at least two side panels that extend from the rim to the front panel, the first tab and the second tab extending from the same side panel.

47. The mask according to claim 43, wherein at least one of the first pleat and the second pleat form a triangular shape.

48. A mask comprising:

a filter layer forming a rim, the filter layer including:

a substantially flat front panel;

a top side panel, a bottom side panel, a right side panel and a left side panel extending from the rim to the front panel;

a first pleat adjoining the front panel; and a first tab and a second tab extending seamlessly from the rim.

49. The mask according to claim 48, further comprising a headstrap attached at the first tab and the second tab.

50. The mask according to claim 48, wherein the first tab and the second tab are generally perpendicular to the front panel when the rim of the mask is pulled open.

51. The mask according to claim 48, wherein the first tab and the second tab extend from the same side panel.

52. A flat-folding mask comprising:

a filter layer forming a rim and having:

a substantially flat front panel spaced from the rim and being substantially centrally positioned;

first and second side panels extending from the rim, a first pleat adjoining the front panel; and a seamless fused portion spaced from the rim, the mask capable of folding substantially flat when not in use, the mask capable of opening for use after being folded flat, the mask when open forming a recess defined by the rim, wherein the first side panel is a top side panel, the second side panel is a bottom side panel, the mask further comprising a right side panel and a left side panel.

53. The mask according to claim 52, further comprising the top and bottom side panel extending from the rim to the front panel.

54. The mask according to claim 52, where the seamless fused portion substantially extends from the rim to the front panel.

55. The mask according to claim 52, further comprising a second pleat, the front panel bridging the first pleat and the second pleat.

56. The mask according to claim 55, wherein the filter layer has an effective center line that bisects the filter layer in a longitudinal direction, the first and second pleats being substantially bisected by the effective center line.

57. The mask according to claim 52, wherein the fused portion includes a first fused portion and a second fused portion positioned within the front panel, the first fused portion and the second fused portion running substantially parallel to each other in a direction longitudinal to the front panel.

58. The mask according to claim 57, wherein the fused portion includes a third fused portion and a fourth fused portion positioned within the front panel, the third fused portion and the fourth fused portion running substantially parallel to each other in a direction latitudinal to the front panel.

59. The mask according to claim 52, wherein the fused portion includes a first fused portion and a second fused portion positioned within the front panel, the first fused portion and the second fused portion running substantially parallel to each other in a direction latitudinal to the front panel.

60. The mask according to claim 52, wherein the fused portion is unpleated.

61. A mask comprising:

a filter layer forming a rim and having:

first and second side panels extending from the rim, a substantially flat front panel spaced from the rim, and a first triangular pleat adjoining the front panel, wherein the first side panel is a top side panel, the second side panel is a bottom side panel, the mask further comprising a right side panel and a left side panel.

62. The mask according to claim 61, wherein the mask is capable of being folded flat for storage.

63. The mask according to claim 61, further comprising a second triangular pleat, the front panel adjoining the first and second triangular pleat.

64. The mask according to claim 61, wherein the triangular pleat is attached to one of the left or right side panel.

65. The mask according to claim 64, wherein the triangular pleat includes a distal end, a top side, and an underside, and wherein the triangular pleat is attached at the distal end to the side panel such that the triangular pleat is open on both the topside and the underside.

66. The mask according to claim 61, wherein the filter layer includes first and second complimentary portions that form the rim and the front panel, the first portion being connected to the second portion at the first and the second seams.

67. The mask according to claim 66, wherein the first and second portions further form the top side panel and the bottom side panel, the top side panel and the bottom side panel extending from the rim to the front panel.

68. The mask according to claim 67, wherein the first and second portions further form the left side panel that includes the first seam and the right side panel that includes the second seam, the first pleat folded over the left side panel, and the second pleat folded over the right side panel.

69. The mask according to claim 68, wherein the first pleat extends from the front panel towards the rim and is attached to the left side panel, and wherein the second pleat forms a second fold that extends from the front panel towards the rim and is attached to the right side panel.

* * * * *